(12) United States Patent
Masi et al.

(10) Patent No.: US 6,495,641 B1
(45) Date of Patent: Dec. 17, 2002

(54) CATALYSTS BASED ON VANADIUM, THEIR PREPARATION AND USE IN THE (CO) POLYMERIZATION OF α-OLEFINS

(75) Inventors: Francesco Masi, Sant' Angelo Lodigiano (IT); Liliana Gila, Cameriano (IT); Roberto Santi, Novara (IT); Antonio Proto, Novara (IT); Evelina Ballato, Crusinallo di Omegna (IT); Anna Maria Romano, Novara (IT)

(73) Assignee: Enichem S.p.A., San Donato Milanese (IT)

( * ) Notice: Subject to any disclaimer, the term of this patent is extended or adjusted under 35 U.S.C. 154(b) by 0 days.

(21) Appl. No.: 09/442,647

(22) Filed: Nov. 18, 1999

(30) Foreign Application Priority Data

Nov. 19, 1998  (IT) .......................................... MI98A2499

(51) Int. Cl.⁷ ................................................. C08F 4/68
(52) U.S. Cl. ..................... 526/169.2; 526/172; 526/189; 526/348; 502/170; 502/171; 502/104
(58) Field of Search ................................ 502/170, 171, 502/104; 526/189, 172, 348, 169.2

(56) References Cited

U.S. PATENT DOCUMENTS 5,502,127 A    3/1996   Bai
5,703,183 A  * 12/1997  Shaffer ........................ 526/189

FOREIGN PATENT DOCUMENTS

| | | | |
|---|---|---|---|
| DE | 26 59 014 A | 7/1977 | |
| EP | 0 684 263 | * 11/1995 | |
| EP | 0 717 050 | 6/1996 | |
| GB | 38 34 130 | 4/1990 | |
| RU | 94011573 | 12/1995 | |
| RU | 2095376 | 11/1997 | |
| SU | 738656 | 6/1980 | |

OTHER PUBLICATIONS

Adisson et al., J. of Polymer Science: Part A; Polymer Chemistry, vol. 32, 1033–1041, 1994.*

Patel et al., Synth. React. Inorg. Met.–Org. Chem., 20(6), 681–692, 1990.*

E. Adisson, et al., "Polymerization of Ethylene at High Temperature by Vanadium–Based Heterogeneous Ziegler–Natta Catalysts. II. Study of the Activation by Halocarbons", Journall Of Polymer Science: Part A: Polymer Chemistry, vol. 32, 1994, pp. 1033–1041.

* cited by examiner

*Primary Examiner*—David W. Wu
*Assistant Examiner*—Ling-Siu Choi
(74) *Attorney, Agent, or Firm*—Oblon, Spivak, McClelland, Maier & Neustadt, P.C.

(57) ABSTRACT

Vanadium complex having general formula (I)

$$(RCOO)_n VX_p L_m \qquad (I)$$

wherein R is a monofunctional hydrocarbon radical having from 1 to 20 carbon atoms and from 1 to 6 halogen atoms, selected from chlorine and bromine, preferably chlorine; X is chlorine or bromine, preferably chlorine; L is an electron donor; p+n=3, 4 or 5, preferably=3; n is greater than or equal to 1; m is between 0 and 3. The preparation of the above complex is also described together with its use in the (co)polymerization of α-olefins.

17 Claims, No Drawings

CATALYSTS BASED ON VANADIUM, THEIR PREPARATION AND USE IN THE (CO) POLYMERIZATION OF α-OLEFINS

The present invention relates to a catalyst based on Vanadium, its preparation and its use in the (co) polymerization of α-olefins.

More specifically, the present invention relates to a catalyst consisting of a Vanadium complex, a co-catalyst based on Al alkyl and, optionally, a reactivator. In addition, the present invention relates to a process for the (co) polymerization of α-olefins in the presence of said catalyst.

At present catalysts based on Vanadium consist of a Vanadium complex, an Al alkyl and a chlorinated reactivator. The Vanadium complex is the precursor of the active species which is formed by interaction with the Al alkyl. This species initiates the polymerization but is also easily deactivated by the same Al alkyl, producing a reduction in activity. The reactivator has the function of re-establishing the active species guaranteeing a longer life-time of the catalyst and consequently a greater catalytic activity (see G. Natta et al., Makromol. Chem., 81, 161–172 (1965; E. Adisson, J. Pol. Sc., art A: Polymer Chemistry, Vol. 31, pages 831–839, 1993). In order to have catalytic activity, however, at least one of the reagents must be chlorinated (see G. Natta et al., J. Polym. Sc., Vol. 51, 411–427, 1961). In fact systems such as $V(acac)_3/AlEt_2Cl$ or $VCl_4/Al(C_6H_{13})_3$ are active in the copolymerization of ethylene with propylene, whereas other systems without chlorine such as $V(acac)_3/Al\ (i-Bu)_3$ and $V(acac)_3/AlMe_3$ do not give a polymer, but become active when a chlorinated reactivator such as $Cl_3CCOOR$, $CCl_4$ is added to the system (see E. Adisson et al. J. Pol. Sc., Part A, Polymer Chemistry, Vol. 32, pages 1033–1041, 1994).

The presence of chlorine in the catalytic system is particularly harmful in the case of the production of ethylene-propylene elastomeric copolymers (EPR and EP(D)M) with a process in suspension which does not comprise a purification phase from the catalytic residues and in particular chlorine. This inevitably causes a lower purity of the products and consequently excludes use in particular applicative fields (for example cables). In addition, the presence of inorganic chlorine in the polymer may develop hydrochloric acid during the processing of the polymer making it necessary to use anti-acid additives, with a consequent increase in the running costs.

The request for catalytically active Vanadium catalysts in the presence of the smallest possible quantity of chlorine, with activities comparable to or higher than those of the known art, therefore remains unsatisfied.

A new group of catalysts capable of giving copolymers containing a small quantity of residual chlorine, has now been found. These catalysts are based on Vanadium complexes having halogenated carboxyl groups as ligands.

A first object of the present invention therefore relates to a Vanadium complex having general formula (I)

$$(RCOO)_n VX_p L_m \qquad (I)$$

wherein R is a monofunctional hydrocarbon radical having from 1 to 20 carbon atoms and from 1 to 6 halogen atoms, selected from chlorine and bromine, preferably chlorine; X is chlorine or bromine, preferably chlorine; L is an electron donor; p+n=3, 4 or 5, preferably=3; n is greater than or equal to 1; m is between 0 and 3.

Examples of R—COO carboxyl groups in formula (I) are selected from:
1) R—COO=

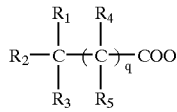

wherein $R_1$, $R_2$, $R_3$, $R_4$ and $R_5$ the same or different, are selected from H, Cl or Br, alkyls, cycloalkyls, aryls, arylalkyls, alkylaryls or alkyls, cycloalkyls, aryls, arylalkyls, alkylaryls containing chlorine or bromine, with the proviso that at least one of the $R_1$–$R_5$ residues is selected from chlorine or bromine, or an alkyl, cycloalkyl aryl, arylalkyl, alkylaryl group containing chlorine or bromine; q varies from 0 to 10.

Non-limiting examples of these derivatives are represented by:
$Cl_3COO$, $CCl_3CH_2COO$, $CCl_3(CH_2)_2COO$, $CHCl_2COO$, $CH_3CCl_2COO$, $C_6H_5CCl_2CH_2COO$, $(C_6H_5)_2CClCOO$, $CH_3CH_2CCl_2COO$, $C_6H_5CH_2CH_2CH_2C$—$HClCOO$, $ClC_6H_4CHClCOO$, $ClC_6H_4CH_2COO$, 2-cyclopropyl-2,2-dichloro-acetic acid.

2) R—COO=

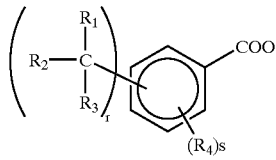

wherein:
$R_1$, $R_2$, $R_3$ and $R_4$, the same or different, are selected from H, Cl or Br, alkyls, cycloalkyls, aryls, arylalkyls, alkylaryls, or alkyls, cycloalkyls, aryls, arylalkyls, alkylaryls containing chlorine or bromine, with the proviso that at least one of the $R_1$–$R_4$ residues is chlorine or bromine or an alkyl, cycloalkyl aryl, arylalkyl, alkylaryl group containing chlorine or bromine;
r and s vary independently from 0 to 5, with the restriction that r+s is from 1 to 5.

Non-limiting examples of these derivatives are represented by:
$Cl_3CC_6H_4COO$, $ClCH_2C_6H_4COO$, $ClCH_2C_6H_2Cl_2COO$, $C_6Cl_5COO$

3) R—COO=

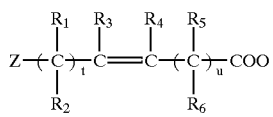

wherein:
Z, $R_1$, $R_2$, $R_3$, $R_4$, $R_5$, $R_6$, the same or different, are selected from H, Cl, Br, alkyl, cycloalkyl, aryl, arylalkyl, alkylaryl, alkyls, cycloalkyls, aryls, arylalkyls, alkylaryls containing chlorine or bromine, with the proviso that at least one of the Z and $R_1$–$R_6$ residues is chlorine or bromine or an alkyl, cycloalkyl aryl, arylalkyl, alkylaryl group containing chlorine or bromine;
t and u independently vary from 0 to 10, preferably from 0 to 2.

Non-limiting examples of these derivatives are represented by:

4) R—COO wherein R is selected from cycloalkyl, polycycloalkyl, cycloalkenyl, polycycloalkenyl having from 3 to 20 C atoms, substituted with at least one chlorine or bromine or with hydrocarbyl groups containing at least one chlorine or bromine.

Non-limiting examples of these derivatives are represented by:
2-chloro-cyclohexane carboxylic acid, 2,2-dichlorocyclopropane-carboxylic acid, 2,2-3,3-tetrachlorocyclopropane-carboxylic acid, perchlorocyclohexane carboxylic acid, cyclo hex-2-ene-2-trichloromethyl-carboxylic acid.

As far as L is concerned, i.e. the electron donor, typical examples are alkyl and cycloalkyl ethers, alkyl esters of aromatic and aliphatic carboxylic acids, aliphatic ketones, aliphatic amines, aliphatic alcohols. L is preferably selected from tetrahydrofuran (THF), dimethoxymethane, diethoxyethane.

A second object of the present invention relates to the process for the preparation of the complexes having general formula (I) which comprises:
a) treatment of a Tallium (Tl) salt having the general formula RCOOTl, wherein R has the meaning defined above, with a Vanadium halide, preferably $VCl_3$, in an aliphatic or aromatic, ether or chlorinated, hydrocarbon solvent, alone or in a mixture, preferably THF and dimethoxyethane, at temperatures ranging from 0 to 50° C., preferably from 15 to 30° C., for a time ranging from 30 minutes to 6 hours, preferably from 1 to 4 hours;
b) separation, preferably filtration, of the Tl halide formed by the reaction;
c) isolation of the Vanadium complex.

In the preferred embodiment, step (c) is carried out by evaporation of the solvent or precipitation of the complex by the addition of a suitable precipitating agent, usually a hydrocarbon solvent, preferably pentane.

Typical but non-limiting examples of these syntheses are provided in the experimental section, which describes, among others, the preparation of $V(CCl_3COO)_3$ by reaction between $VCl_3$ and $Tl(CCl_3COO)$ in a molar ratio 1/3, $V(CH_2Cl—C_6H_4—COO)_3$ by reaction between $VCl_3$ an $CH_2Cl—C_6H_4—COOTl$ in a molar ratio 1/3, $V(CCl_3COO)_2Cl$ by reaction between $VCl_3$ and $Tl(CCl_3COO)$ in a molar ratio 1/2, $V(CCl_3CH_2CH_2COO)_3$ by reaction between $VCl_3$ and $CCl_3CH_2CH_2COOTl$ in a ratio 1/3.

A third object of the present invention relates to a catalytic system for the (co)polymerization of α-olefins consisting of:
(a) Vanadium complex having general formula (I),
(b) organo Aluminum derivative having general formula (II) $AlR_nX_m$, wherein R is a $C_1$–$C_{20}$ alkyl group, X is chlorine or bromine, preferably chlorine, and n+m=3, with the exclusion of the compound having n=0,
(c) optionally a reactivator, preferably chlorinated. Among the Vanadium compounds having general formula (I), those wherein RCOO has general formula (Ia)

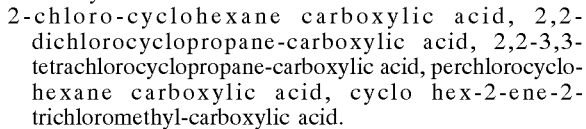

wherein n is an integer between 0 and 2, i.e. trichloroacetate (n=0), trichloropropionate (n=1), trichlorobutyrrate (n=2), have proved to be particularly effective.

Typical examples of compounds having general formula (II) are $AlEt_2Cl$ (diethylchloroaluminum), $AlMe_3$ (trimethylaluminum), $AlEt_3$ (triethylaluminum), Al (i-Bu)$_3$ (triisobutylaluminum).

In the preferred embodiment the cocatalyst having general formula (II) has a $C_1$–$C_{20}$ alkyl group as R, n=3 and m=0. Even more preferably R is an isobutyl group.

The molar ratio between said cocatalyst having general formula (II) and the catalyst having general formula (I) is between 1 and 500, preferably between 3 and 100, more preferably between 20 and 50.

When, in the cocatalyst having general formula (II), m is different from 0, the preferred cocatalyst is diethylchloroaluminum. When, in the cocatalyst having general formula (II), m=0, the preferred cocatalyst is triisobutylaluminum. In the preferred embodiment the molar ratio cocatalyst and catalyst is between 5 and 10.

As far as the reactivator is concerned, this is usually selected from chlorinated organic compounds, for example ethyl trichloroacetate, n-butyl perchlorocrotonate, diethyl dichloromalonate, carbon tetrachloride, chloroform.

The molar ratio between the possible reactivator and vanadium can vary from 0:1 to 100:1, preferably from 1:1 to 40:1, even more preferably between 1:1 and 10:1.

When, in the cocatalyst having general formula (II), m is different from 0, the preferred reactivator is ethyl trichloroacetate and the preferred molar ratio between reactivator and vanadium is between 4:1 and 10:1.

When, in the cocatalyst having general formula (II), m is equal to 0, the preferred reactivator is carbon tetrachloride and the preferred molar ratio between reactivator and vanadium is between 10:1 and 50:1.

In the preferred embodiment the reactivator is not used.

The catalysts of the present invention can be used in (co)polymerization processes of α-olefins in liquid phase (solution or suspension) at low or medium pressure (15–50 ate) and at temperatures ranging from −5 to 75° C.

In the preferred embodiment the temperature is between 25 and 60° C. and the pressure between 6 and 35 ate.

The polymers and copolymers thus obtained have very high average molecular weights. If the molecular weight is to be regulated to a lower value, hydrogen can be used as molecular weight regulator.

The catalyst for the (co)polymerization of α-olefins and terpolymerization with dienes is prepared by contact of the Al alkyl with the V complex dissolved in an aliphatic or aromatic hydrocarbon solvent and, optionally, with the reactivator. The contact can take place separately without the mixture of olefins to be polymerized for a time ranging from 1 minute to 30 minutes, preferably from 5 to 20 minutes, at a temperature ranging from 0° C. to 50° C., preferably from 15° C. to 40° C., or it can take place in the polymerization reactor in the presence of the mixture of monomers. In this case the three reagents can be added separately or as a mixture of two of these. The catalyst is preferably formed "in situ" by introducing the Al alkyl into the autoclave already containing the solvent (heptane or liquid propylene), the reagent mixture and, optionally, the termonomer and adding the solution of V complex with the possible reactivator in toluene.

The catalysts of the present invention can be used in the polymerization of α-olefins, preferably in the polymerization of ethylene, in the copolymerization of ethylene with propylene and higher α-olefins and in the terpolymerization of ethylene with propylene and dienes to give polymers with a density ranging from 0.96 g/cm$^3$ and 0.86 g/cm$^3$.

The copolymerization of ethylene-propylene to give EPR elastomeric copolymers and the terpolymerization of ethylene-propylene-non-conjugated diene to give EP(D)M rubbers, are particularly preferred.

The diene can be selected from:
alicyclic dienes with a linear chain such as 1,4-hexadiene and 1,6-octadiene;
acyclic dienes with a branched chain such as 5-methyl-1,4-hexadiene, 3,7-dimethyl-1,6-octadiene, 3,7-dimethyl-1,7-octadiene;

alicyclic dienes with a single ring such as 1,4-cyclohexadiene, 1,5-cyclo-octadiene;
dienes having condensed and bridged alicyclic rings such as methyltetrahydroindene, 5-ethylidene-2-norbornene (ENB), 5-propenyl-2-norbornene.

In the preferred embodiment the diene is ENB or 1-methylene-2-vinyl-cyclopentane.

The EPR and EP(D)M elastomeric copolymers which can be obtained with the catalysts of the present invention contain from 20 to 65% in moles of propylene and quantities not exceeding 15% of ENB. The weight average molecular weight of the polymer obtained in the presence of hydrogen varies from 50,000 to 500,000.

The following examples provide a better illustration of the present invention.

EXAMPLES

The characterization by means of $^1$H-NMR spectroscopy, mentioned in the following examples, was carried out with a Bruker MSL-200 spectrometer.

The characterization by means of FTIR spectroscopy was carried out on a Perkin-Elmer 1800 FTIR spectrometer with 4 cm$^{-1}$ resolution and 64 scannings.

The determination of the Vanadium was carried out on a Perkin-Elmer Plasma II inductively coupled plasma spectrometer (ICP) with atomic emission detection (AES).

The determination of the total chlorine was carried out with a Philips PW 1404/10 sequential X-ray fluorescence spectrometer (XRF) with an Sc/Mo double anode tube.

The total chlorine was obtained from the sum of the inorganic chlorine (i.e. chlorine bound to V and/or Al) and organic chlorine (i.e. chlorine bound to a hydrocarbyl residue).

The measurement was carried out on alcoholic solutions of the Vanadium complex diluted with MilliQ water at 2% by weight of $HNO_3$ in a ratio of 1:100 for the determination of V and 1:1 for that of chlorine. The concentrations of V and Cl were calculated on the basis of a calibration curve obtained with reference solutions with a known titer of the element to be determined (V or Cl) and having a composition identical to that of the samples (water, EtOH, $HNO_3$).

The determination of inorganic Cl was carried out potentiometrically using a Titroprocessor 670 and an Ag electrode (cod. 6.0404.000) filled with a saturated solution of $KNO_3$ (both Metrohm). The alcoholic solution of the sample was acidified with $H_2SO_4$ 3M and titrated with $AgNO_3$ 0.1N.

The molecular weight measurement was effected by Gel-Permeation chromatography (GPC). The analyses of the samples were carried out in 1,2,4-trichlorobenzene (stabilized with N,N'-m-phenylenedimaleimide) at 135° C. with a WATERS 150-CV chromatograph using a Waters differential refractometer as detector. The chromatographic separation was obtained with a set of $\mu$Styragel HT columns (Waters) with pore dimensions of $10^3$, $10^4$, $10^5$ and $10^6$ A, establishing a flow-rate of the eluant of 1 ml/min.

The data was obtained and processed by means of Maxima 820 software version 3.30 (Millipore). The calibration curve used for calculating the number (Mn) and weight (Mw) average molecular weight was obtained using standard samples of polystyrene with molecular weights within the range of 6,500,000–2,000 and applying the Mark-Houwink equation valid for linear polyethylene and for polypropylene; the molecular weight values were corrected in relation to the composition of the polymer using the Scholte equation.

The propylene content in the ethylene-propylene copolymers was determined on samples in the form of films using a Perkin-Elmer 1800 FTIR spectrometer with 4 cm$^{-1}$ resolution and 64 scannings, measuring the band absorptions at 4390 and 4255 cm$^{-1}$, in the ethylene-propylene-ENB terpolymers by measuring the bands at 4390, 4330, 4255 and 1688 cm$^{-1}$ and on the basis of calibration curves prepared with copolymers and terpolymers respectively with a known composition.

Example 1

Synthesis of the Comparative Catalyst (I) V $(CCl_3$—CO—CH—CO—$CH_3)_3$ 3 g (15 mmoles) of acetylacetone ($CH_3$—CO—$CH_2$—CO—$CH_3$) are added to an aqueous solution of $Na_2CO_3$ (0.79 g, 75 mmoles in 100 ml); the mixture is left under vigorous stirring for 15 minutes at room temperature. 100 ml of chloroform are then added and a solution of $VCl_3$ obtained by dissolving 0.79 g (5 mmoles) of the product in 50 ml of water are added dropwise. The mixture is left under stirring at room temperature for two hours; the organic phase becomes brown-coloured, whereas the aqueous phase remains colourless. The organic phase is separated and the solvent evaporated. 2.9 g of a light-brown solid are obtained.

Yield: 90%; V: 7.48%; Cl: 44%; Cl/V=8.6; $^1$H-NMR (in $C_6D_6$, δ in ppm): cis isomer—56.8 ppm ($CH_3$); 44 ppm (CH): trans isomer—73, 61, 54 ppm ($CH_3$); 65, 51, 35 ppm (CH).

Example 2

Synthesis of the Catalyst $V(CCl_3COO)_3(THF)_n$,

2a) Synthesis of Tallium Trichloride Acetate—Tl ($CCl_3COO$)

5.1 g of solid $CCl_3COOH$ (0.031 moles) are added to a suspension of 7.0 g of $Tl_2CO_3$ (0.0149 moles) in 100 ml of methanol, maintained under stirring. The mixture is left under stirring at room temperature. The solution is then filtered and the filtrate is evaporated at 15° C. and 20 mmHg. The solid obtained is washed with ethyl ether (10×50 ml) and dried at $10^{-3}$ mmHg. 10.1 g of tallium trichlorbacetate in the form of a white solid are obtained.

Yield: 92%; IR (in nujol): 1540 cm$^{-1}$ ($v_{-co}$).

2b) Synthesis of the Vanadium Complex (II) V $(CCl_3COO)_3$ $(THF)_1$ 8.43 g (23 mmoles) of $TlCCl_3COO$ dissolved in 70 cc of THF are slowly added to a solution obtained by dissolving 2.86 g (7.7 mmoles) of $VCl_3$ $(THF)_3$ (Aldrich—97%) in 60 ml of THF. The reaction, carried out for 4 hours at room temperature, takes place with the precipitation of a white solid (TlCl) and a colour change from red to greenish-brown. The precipitate is filtered, the solvent is evaporated and dried under vacuum. 4.5 g of a bright green solid are obtained. Yield: 97%; V: 7.98%; Cl: 50%; Cl/V=9.1; IR (nujol): 1600–1800 cm$^{-1}$ ($v_{asym}CO_2$); 1403 cm$^{-1}$, 1263 cm$^{-1}$ ($v_{sym}CO_2$).

2c) Synthesis of the Catalyst IIa $V(CCl_3COO)_3$ $(THF)_{1.9}$ 84 g (228 mmoles) of $TlCCl_3COO$ dissolved in 300 ml of THF are slowly added to a solution obtained by dissolving 28.5 g (76.2 mmoles) of $VCl_3$ $(THF)_3$ (L. E. Manzer, Inorg. Synthesis, 21, 135, (1982)) in 300 ml of THF. The reaction is carried out for 4 hours at room temperature; TlCl precipitates and the suspension initially red becomes green. The precipitate is filtered and the solvent evaporated. The product obtained is further dissolved in 200 ml of THF and 600 ml of pentane and cooled to −40° C. for two hours. A solid precipitates which is filtered, washed with pentane and dried at room temperature for 30 hours. 47.5 g of green product are obtained.

Yield: 91%; V: 7.42%; Cl: 47.9%; Cl/V=9.3; THF/V=1.88 ($^1$H-NMR; $CD_3CN$); IR (nujol): 1650–1800 $cm^{-1}$ ($v_{asym.}CO_2$) 1263 $cm^{-1}$ ($v_{sym.}CO_2$);

2d) Synthesis of the Catalyst (IIb) $V(CCl_3COO)_3$ 400 mg of the catalyst (IIa) are dissolved in about 20 ml of toluene. After a few minutes a precipitate begins to separate from the solution. The suspension is left to rest for 4 days at room temperature; it is then filtered and the solid is dried under vacuum, obtaining 200 mg of a light green solid.

Yield: 50%; V: 9%; Cl: 57.1%; Cl/V=9.3; THF=($^1$H-NMR; $CD_3CN$): traces; IR (nujol): 1645 $cm^{-1}$ ($v_{asym}CO_2$); 1403 $cm^{-1}$ ($v_{sym.}CO_2$).

Example 3

Synthesis of the Catalyst (III) $V(CH_2Cl—C_6H_4—COO)_3$ 0.92 g (5.8 mmoles) of $VCl_3$ (Aldrich—97%) in 150 ml of toluene are suspended in a 500 ml flask; a suspension of 3-chloromethylbenzoic acid ($CH_2Cl—C_6H_4—COOH$, Fluka) in toluene (3 g, 17.6 mmoles in 50 ml of solvent) are added. Gaseous $NH_3$ is bubbled in for about 2 hours; the initial purple suspension becomes brown. After reflux heating for 5 hours, the suspension becomes green. It is filtered to separate the ammonium chloride formed and the filtrate is evaporated under vacuum. 1 g of green product is obtained.

Yield: 30%; V: 8.39%; Cl: 16.4; Cl/V=2.9.

Example 4

Synthesis of the Catalyst (IV) $V(CCl_3COO)_2Cl$ $(THF)_1$ 3.7 g (10 mmoles) of $VCl_3$ $(THF)_3$ (Aldrich—97%) are dissolved in 100 ml of THF. 7.3 g (20 mmoles) of $CCl_3COOTl$ dissolved in 80 cc of THF are slowly added (in about 3.5 hours) to the resulting solution. The reaction is carried out for 1 hour at room temperature. A precipitate is formed (TlCl) and the suspension changes colour passing from red to brown. The precipitate is filtered, the solvent is evaporated and the solid dried under vacuum. The solid recovered is washed three times with pentane (50 ml each time), is filtered and dried with a pump. 4 g of brown solid are obtained.

Yield: 83%; V: 10.54%; $Cl_{tot.}$: 51.35%; $Cl_{inorg.}$: 7.33%; $Cl_{tot.}/V=7$; $Cl_{inorg}/V=1$.

Example 5

Synthesis of the Catalyst (V)—V $(CCl_3CH_2CH_2COO)_3$ $(THF)_1$

5a) Synthesis of 4,4,4-Trichloro-butyro-nitrile (Bruson H. A. et al. J.Am.Chem.Soc.67, 601, (1945))

242 ml of $CHCl_3$ (3.02 mmoles), 36.0 g of $[C_6H_5CH_2N]^+$ $[(CH_3)_3Cl]^-$ (0.196 moles, BTMACl) and 11.0 g of KOH (0.196 moles) in 27 ml of water are charged into a three-necked flask equipped with a mechanical stirrer, drip funnel and two-lined fitting connected to a stream of nitrogen, and a thermometer. After cooling to 0÷5° C. by means of a cryostat, 300 ml of $CH_2$=CHCN (4.56 moles) are added in about three hours. The mixture is left under stirring at this temperature for 24 hours. The reaction mixture is washed three times with water. The aqueous phase is extracted with ethyl ether. The ether phase and chloroform phase are joined and concentrated. The mixture is distilled collecting the fraction which passes to 91÷103° C. (16 mm of Hg). The distillate obtained which solidifies in the flask weighs 91.0 g.

Yield: 17%; $^1$H NMR (in $CDCl_3$, δ in ppm) 3.08 (2H, t), 2.85 (2H, t). IR (in nujol): 2260 $cm^{-1}$ ($v_{-CN}$).

b) Synthesis of 4,4,4-Trichloro-butyric Acid 40.5 gr of 4,4,4-trichloro-butyronitrile (0.236 moles) and 170 ml of concentrated HCl are charged into a 250 ml flask. The mixture is left under stirring at 60° C. for six hours. The solid acid precipitates and is filtered, washed with water and dried with a mechanical pump. 43.4 g of 4,4,4-trichlorobutyric acid are obtained.

Yield: 97%; Melting point: 54.8° C. (read. 55° C.). $^1$H NMR (in $CDCl_3$, δ in ppm): 10.82 (1H, s broad) 3.15 (2H, t), 2.92 (2H, t). IR (in nujol): 3260 $cm^{-1}$ ($v_{-OH}$), 1720 $cm^{-1}$ ($v_{-CO}$).

c) Synthesis of Tallium 4,4,4-Trichloro Butyrate

A solution of 12.0 g of $CCl_3CH_2CH_2COOH$ (0.063 moles) in 20 ml of methanol are added to a suspension of 12 g of $Tl_2CO_3$ (0.026 moles) in 100 ml of methanol, maintained under stirring. The mixture is further diluted with 50 ml of methanol and is left under stirring for 2 hours at room temperature. The solution is then filtered and the filtrate is evaporated at 20° C. and 20 mmHg. The solid obtained is washed with ethyl ether (10×50 ml) and dried at $10^{-3}$ mmHg. The tallium salt obtained as a white solid weighs 17.6 g.

Yield: 86%; $^1$H NMR (in $CD_3OD$, δ in ppm): 3.01 (2H, t), 2.62 (2H, t) IR (in nujol): 1540 $cm^{-1}$ ($v_{-CO}$).

d) Synthesis of the Vanadium Complex (V)

3.19 g of $VCl_3$. $(THF)_3$ (8.54 mmoles) dissolved in 160 ml of anhydrous THF are charged into a three-necked, 250 ml flask. 10.11 g of solid $CCl_3CH_2CH_2COOTl$ (26.61 mmoles) are slowly added. The solution changes colour (from clear red to dark green). The solution is left under stirring for about 4 hours. It is filtered and the green filtrate is evaporated under vacuum. The resulting solid is dried at $10^{-3}$ mmHg for 24 hours. 4.44 g of complex are obtained.

Yield: 75%; V: 7.55%; Cl: 50.2%; Cl/V: 9.5.

Example 6

Synthesis of the Catalyst (VI)—$V(CHCl_2COO)_3$ $(THF)_1$ a) Synthesis of Tallium Dichloro Acetate—Tl $(CHCl_2COO)$ A solution of 3.5 ml of $CCl_2HCOOH$ (0.045 moles) in 20 ml of methanol are added to a suspension of 9.37 g of $Tl_2CO_3$ (0.020 moles) in 100 ml of methanol, maintained under stirring. The mixture is diluted with 50 ml of methanol and is left under stirring for 2 hours at room temperature. The solution is then filtered and the filtrate is evaporated at 15° C. and 20 mmHg. The solid obtained is washed with ethyl ether (10×50 ml) and dried at $10^{-3}$ mmHg. The tallium salt obtained as a white solid weighs 10.2 g.

Yield: 76%; $^1$H NMR (in $CD_3OD$, δ in ppm): 5.93 (1H, s). IR (in nujol): 1580 $cm^{-1}$ ($v_{-CO}$).

b) Synthesis of the Vanadium Complex (VI)

3.21 g of $VCl_3.(THF)_3$ (0.00863 moles) in 250 ml of anhydrous THF are charged, under argon, into a 500 ml test-tube and 8.58 g of $Tl(CCl_2HCOO)$ (0.02589 moles) are added. After 15 hours, the TlCl is filtered and washed with THF. The solvent is evaporated and the solid is dried with a mechanical pump at 50° C., owing to the difficulty in solidifying of the green residue. 26 g of complex are obtained.

Yield: 59%; V: 10.06%; Cl: 37.5%; Cl/V=5.4.

Example 7

Synthesis of the Catalyst (VII)—V(CCl₃CH₂COO)₂Cl (THF)₁ a) Synthesis of 2,4,4,4-Tetrachlorobut-1-ene

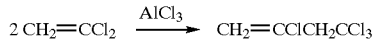

$$2\ CH_2{=}CCl_2 \xrightarrow{AlCl_3} CH_2{=}CClCH_2CCl_3$$

80 ml of 1,2-dichloroethane and 166.6 ml of 1,1-dichloroethylene 2.46 moles) are charged into a three-necked flask equipped with a mechanical stirrer, a fitting connected to a stream of nitrogen, and a thermometer. The mixture is cooled to −70° C. and 14 g of anhydrous AlCl₃ (0.105 moles) are added. The temperature is slowly brought to −25° C. and the mixture is left under stirring for 8 hours. The solution becomes a dark blue colour. It is then hydrolyzed with water and ice and the temperature is prevented from exceeding −20° C. It is extracted with methylene chloride, washed with water until neutrality and dried on Na₂SO₄. The excess solvent is distilled at 30° C. and 20 mmHg. The residue is distilled at 0.9 mmHg. 53.0 g of product are obtained.

Yield: 22.3%; ¹H NMR (in CDCl₃, δ in ppm): 5.6 (1H, t), 5.55 (1H, t) 3.67 (2H, s).

b) Synthesis of 3,3,3-Trichloropropionic Acid $$CCl_3CH_2CCl{=}CH_2 \xrightarrow{MnO_4^-} CCl_3CH_2COOH$$

6 g of tetrachlorobutene, 1 g of sodium carbonate, 250 ml of water and 13.7 g of potassium permanganate are charged into a 750 ml flask equipped with a mechanical stirrer and thermometer. The whole mixture is left under stirring and the temperature is maintained at about 45° C. with water and ice. 6 g of tetrachlorobutene and 13.7 g of KMnO₄ are subsequently added at regular intervals of 15 minutes, five times until a total of 30 g of tetrachlorobutene has been added.

54.0 g of sodium bisulfite are then added together with sufficient dilute sulfuric acid as to have a transparent solution. The solution is extracted with ethyl ether, washed with water, dried on sodium sulfate and the solvent is evaporated. 15.0 g of acid are obtained as a yellowish solid.

Yield: 45%; ¹H NMR (in CDCl₃, δ in ppm): 10.50 (1H, s broad) 3.83 (2H, s).

c) Synthesis of Tallium 3,3,3 Trichloro Propionate—Tl (CCl₃CH₂COO)

5.14 g of solid 3,3,3-trichloropropionic acid (0.029 moles) are added to a suspension of 6.80 g of Tl₂CO₃ (0.0145 moles) in 100 ml of methanol, maintained under stirring. The mixture is left under stirring for 1 night at room temperature. The solution is then filtered and the filtrate evaporated at 15° C. and 20 mmHg. The solid obtained is washed with ethyl ether (10×50 ml) and dried at 10⁻³ mmHg. 10.05 g of tallium salt are obtained in the form of a white solid.

Yield: 89.6%; ¹H NMR (in CD₃OD, δ in ppm): 4.85 (2H, s).

d) Synthesis of the V Complex (VII)

2.5 g (0.0067 moles) of crystalline VCl₃, 7.34 g (0.019 moles) of CCl₃CH₂COOTl and THF to dissolve the whole mixture, are charged into a 500 ml test-tube. The mixture is maintained under stirring for about 15 hours. It is then filtered, the filtrate is dried under vacuum and the green solid formed weighs 5.12 g.

Yield: V: 9.84%; Cl: 43.5%; Cl/V=6.3.

Example 8

Synthesis of the Catalyst (VIII)—V(CH₃CCl₂COO)₃ (THF)₂ a) Synthesis of Tallium 2,2 Dichloro Propionate—Tl (CH₃CCl₂COO)

6.83 g of 2,2-dichloropropionic acid (0.0477 moles) are added to a suspension of 11.28 g of Tl₂CO₃ (0.0248 moles) in 180 ml of methanol, maintained under stirring. The mixture is left under stirring for 1 night at room temperature. The solution is then filtered and the filtrate evaporated at 15° C. and 20 mmHg. The solid obtained is washed with ethyl ether (10×50 ml) and dried at 10⁻³ mmHg. 15.05 g of tallium salt are obtained in the form of a white solid.

Yield: 93.8%; ¹H NMR (in CD₃OD, δ in ppm): 4.5 (3H, s).

d) Synthesis of the V Complex (VIII)

1 g of VCl₃. (THF)₃ (2.66 mmoles) dissolved in 60 ml of anhydrous THF CH₃CCl₂COOTl is charged into a 150 ml test-tube, under argon. 2.81 g of solid (8.06 mmoles) are slowly added. The solution changes colour. It is left under stirring for about 4 hours and is then filtered. The green solution is evaporated from the solvent and the resulting solid is dried at 10⁻³ mmHg for 24 hours. 1.29 g of complex are obtained.

Yield: 87%; V: 8.21%; Cl: 30.7%; Cl/V=5.4.

Example 9

Synthesis of the Catalyst (IX)—V (CCl₃CH=CHCOO)₃ (THF)₁ a) Synthesis of 4,4,4-Trichloro-but-2-enoic Acid

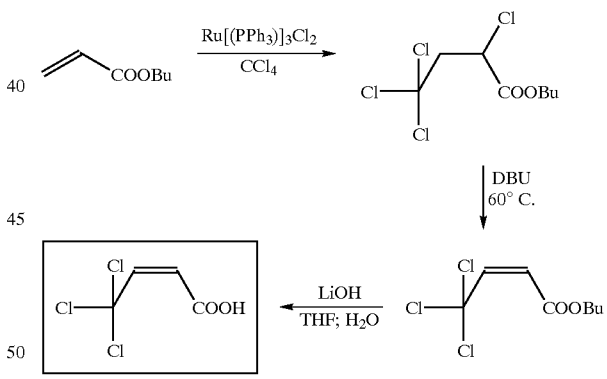

Synthesis of Tris (Triphenylphosphine)ruthenium Dichloride

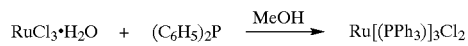

$$RuCl_3{\cdot}H_2O + (C_6H_5)_2P \xrightarrow{MeOH} Ru[(PPh_3)]_3Cl_2$$

0.5 g of RuCl₃.H₂O are dissolved under argon in 150 ml of anhydrous methanol and the solution is refluxed for 5 minutes. It is then brought to room temperature and 2.3 g of triphenylphosphine are added. It is then brought to reflux temperature again for three hours. The solution is subsequently cooled to room temperature, the solid obtained is filtered and dried with a mechanical pump.

Synthesis of Butyl 4,4,4,2-Tetrachlorobutenoate

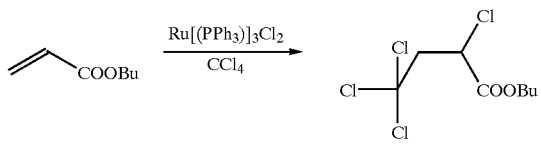

12 g of butylacrylate (94 mmoles), 200 mg of RuCl$_2$[PPh$_3$]$_3$ and 28 ml of carbon tetrachloride are charged into a 500 ml flask under argon. The mixture is brought to 90° C. for about 4 hours. The completion of the reaction is observed by means of GC control. The mixture is cooled, petroleum ether is added and the triphenylphosphine which precipitates, is filtered. The solvent is evaporated and 13 g of raw product are obtained which is used directly in the subsequent step.

Synthesis of Butyl 4,4,4-Trichloro-but-2-enoate

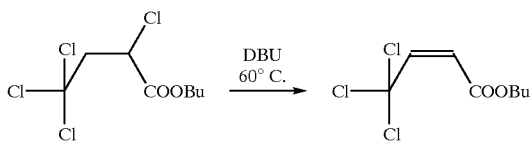

6 g of butyl 4,4,4,2-tetrachloro butanoate (22.4 mmoles) in 20 ml of anhydrous toluene are charged into a 250 ml flask under inert gas and 5 ml of 1,8-diazabi cyclo[5.4.0]undecan-7-ene (DBU) are added with exothermy. The temperature is brought to 60° C. for 3 hours. The completion of the reaction is observed by means of GC control; the mixture is cooled, water is added, the mixture is extracted with ethyl ether and anhydrified on Na$_2$SO$_4$. The residue obtained after evaporation of the solvent and purified by chromatography on silica gel (eluant: hexane/ethyl acetate=9/1) weighs 4 g.

Yield: 76%;

Synthesis of 4,4,4-Trichloro-but-2-enoic Acid

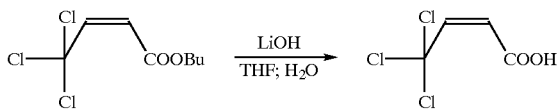

17.82 g of LiOH in 20 ml of water are added to a solution containing 3 g of butyl 4,4,4-trichloro-but-2-enoate (0.0128 moles) in 300 ml of THF. The mixture is stirred for 1 hour at room temperature. It is then brought to pH neutral with the addition of HCl 1N, extracted with ethyl acetate and anhydrified on Na$_2$SO$_4$. The solid obtained after evaporation of the solvent at reduced pressure and washing with petroleum ether weighs 2.1 g.

Yield: 87%.

b) Synthesis of Tallium 4,4,4-Trichloro-but-2-enoate—Tl (CCl$_3$CH=CHCOO)

1.56 g of 4,4,4-trichloro-but-2-enoic acid (8.4 mmoles) are added to a suspension of 1.94 g of Tl$_2$CO$_3$ (4.2 mmoles) in 80 ml of methanol, maintained under stirring. The mixture is left under stirring for 4 hours at room temperature. The solution is then filtered and evaporated at 15° C. and 20 mmHg. The solid obtained is washed with ethyl ether (10×50 ml) and dried at 10$^{-3}$ mmHg. 3.0 g of tallium salt are obtained in the form of a white solid.

Yield: 91.2%.

c) Synthesis of the Vanadium Complex (IX)

0.80 g of VCl$_3$.(THF)$_3$ (2.15 mmoles) dissolved in 60 ml of anhydrous THF are charged into a 150 ml test-tube, under argon. 3 g of CCl$_3$CH=CHCOOTl (6.54 mmoles) are slowly added. The solution changes colour. It is left under stirring for about 4 hours and is then filtered. The green solution, after being washed, is evaporated from the solvent and the resulting solid is dried at 10$^{-3}$ mmHg for 24 hours. 1.40 g of complex are obtained.

Yield: 95%; V: 7.12%; Cl: 40.5%; Cl/V=9.3.

Example 10

Synthesis of the Catalyst (X) V(o-Cl, m-Cl—C$_6$H$_3$—CH$_2$—COO)$_3$

A suspension of 2,4-dichlorophenylacetic acid (Acros) in toluene (11.3 g, 55 mmoles in 150 ml of solvent) is added by siphoning to a suspension of VCl$_3$ (Aldrich-97%) in toluene (2.9 g, 18.2 mmoles in 100 ml of solvent). Gaseous NH$_3$ is bubbled into the reaction mixture for 2 hours; a white solid is formed (ammonium salt of the acid) and the suspension changes colour from purple to brown. The mixture is then heated to reflux temperature for 5 hours; the suspension becomes green. Its volume is reduced by evaporation under vacuum, and it is then filtered to separate the ammonium chloride formed. Upon evaporation of the filtrate, 12 g of a solid bright-green product are obtained.

Yield: 100%; V: 7.82%.

Example 11

Copolymerization of Ethylene-propylene in Solution

Vacuum-nitrogen is applied for at least three times at 90° C. and for a total duration of about 2 hours, to a Buchi autoclave with a 2 l steel reactor equipped with a burette for moving the catalyst, a propeller stirrer, a thermocouple and heating jacket connected to a thermostat for the temperature control. Before each test a flushing of the reactor is effected by maintaining under stirring at 90° C. a solution containing 500 ml of anhydrous heptane and 5 ml of Al(i-Bu)$_3$ for about two hours. The contents of the reactor are discharged by means of a valve situated on the bottom under light nitrogen pressure and a solution containing 1 l of heptane and aluminum alkyl of the type and in such a quantity as to respect the desired Al/V ratio. The autoclave is pressurized introducing in order 0.2 ate. of hydrogen, 200 g of propylene (4.9 ate.) and 7 g of ethylene (1 ate.) and the whole mixture is thermostat-regulated at 30° C. At this stage, a solution of the vanadium complex obtained by dissolving 0.042 mmoles in 10 ml of toluene and, optionally, the reactivator of the type and in such a quantity as to respect the desired reactivator/Vanadium ratio, is introduced applying a slight overpressure of nitrogen, by means of the burette situated at the head of the autoclave. Once the catalyst has been introduced, the system is left for the desired time maintaining a constant pressure by means of a stream of ethylene. At the end the contents of the reactor are discharged under pressure by means of the valve on the bottom and coagulated in about 3 l of ethanol. The polymer is separated by filtration, washed with acetone and anhydrified under vacuum at 40° C. for about 8 hours.

Example 12

Copolymerization of Ethylene-propylene-ENB in Liquid Propylene

The polymerization is carried out in an 0.5 litre pressure reactor, equipped with a magnetic drag anchor stirrer and external jacket connected to a heat exchanger for the temperature control. The reactor is previously flushed maintaining it under vacuum (0.1 Pascal) at a temperature of 80° C. for at least 2 h. At 23° C. 120 g of liquid "polymerization grade" propylene and optionally hydrogen and the diene (ENB) are fed to the reactor in the quantities indicated in tables 6 and 7. The reactor is then brought to the polymerization temperature of 40° C. and the desired quantity of aluminum alkyl is introduced; "polymerization grade" gaseous ethylene is then fed, by means of a plunged pipe, until the desired equilibrium pressure is reached (20–22 ate.). Under these conditions the molar concentration of ethylene in the liquid phase is between 8 and 12% depending on the total pressure of the system. Finally the desired quantity of solution (suspension) of vanadium salt in toluene is transferred under a stream of inert gas to a metal container from which, by means of an overpressure of nitrogen, it is charged into the reactor.

The polymerization reaction is carried out at 40° C., care being taken that the total pressure is kept constant by continuously feeding ethylene to compensate the part which has reacted. After 1 h the ethylene feeding is interrupted and the polymerization is stopped by rapid degassing of the residual monomers. The polymer is recovered, after being washed with ethyl alcohol and dried at 60° C., 1 Pascale for at least 8 h.

Commments on the Tables

Tables 1–5 indicate the results of copolymerization tests of ethylene-propylene in solvent in the presence of $H_2$, whereas tables 6 and 7 refer to co- and ter-polymerization tests of ethylene-propylene-diene in liquid propylene carried out both in the presence of and without $H_2$. The comparative examples refer to tests carried out in the presence of V complexes with acetylacetonic and chlorinated acetylacetonic ligands—V($CH_3$—CO—CH—CO—$CH_3$)$_3$ and V($CCl_3$—CO—CH—CO—$CH_3$)$_3$, known catalysts in the polymerization of EP(D)M.

From the data of Table 1 it can be observed how the catalysts of the present invention (from II to V) in the presence of DEAC and ETA form a catalytic system which is analogous (as far as the catalytic activity is concerned both with respect to Vanadium and to chlorine and the characteristics of the polymer) to that based on V(acac)$_3$.

From the data of Table 2 it can be seen that the catalysts of the present invention (from II to V) are more active, in the presence of Al trialkyls, than both V(acac)$_3$, which does not have a catalytic activity, and also V trichloroacetylacetonate—V($CCl_3$—CO—CH—CO—$CH_3$)$_3$—, which gives an amount of polymer as much as 20 times lower. In addition, the activity of the catalysts of the present invention is not modified by the presence of the reactivator which, on the other hand, is indispensable for making V(acac)$_3$ active (Table 3).

The molecular weights (Mw) of the polymers vary frm 200 to 400,000; the MWD is generally quite wide, even reaching values of 11, but can be limited to values of about 3–6 in various ways:

by varying the quantity of THF coordinated to V (Table 4);

by lengthening the aliphatic chain of the chlorocarboxylic ligand (from $CCl_3COO$— to $CCl_3CH_2CH_2COO$—) (Table 2, examples 9 and 12);

by subjecting the V complex to aging with the Al alkyl under certain temperature conditions and Al/V ratio (Table 5).

With respect to the industrial system V(acac)$_3$/AlEt$_2$Cl/ETA (comp. example 1 —Table 1), the catalytic systems consisting of the catalysts of the present invention and Al(i-Bu)$_3$ demonstrate, in the tests in solution, a catalytic activity which, with respect to Vanadium, is comparable or even lower, but which with respect to chlorine is always higher (from 2 to 12 times); they give a polymer with a lower % of incorporated $C_3$ (from about 35% to 20–30% in moles), with higher molecular weights (Mw) (from about 100,000 to 400,000) and a wider MWD (from 2 to at least 4–5).

The catalysts of the present invention have analogous behaviour in liquid propylene.

With respect to the reference industrial system V(acac)$_3$/AlEt$_2$Cl/ETA, in fact, the catalytic system of the present invention—V(OCOCCl$_3$)$_3$(THF)$_2$/Al (i-Bu)$_3$-demonstrates, in the tests in liquid propylene (Tables 6 and 7), a catalytic activity which is comparable with respect to V, but which is higher (from 2 to 8 times) with respect to chlorine; it gives a polymer with a lower % of incorporated $C_3$ (from about 50 to 20–35% by weight), with a higher % of incorporated ENB (from 3.5 to 6–7% by weight), with higher molecular weights (Mw). These pass from 700,000–1,000,000 to values >1,000,000 (no longer measurable with GPC) for the polymers obtained from the tests carried out without $H_2$, and reach values of up to 300,000 for the polymers obtained from the tests carried out in the presence of $H_2$.

From the tests carried out in the presence of $H_2$, however, polymers are obtained with a lower yield than that obtained from tests carried out without $H_2$, whereas the quantity of incorporated comonomer and termonomer remains the same. It should be noted however, that even with a smaller quantity of polymer produced, the activity with respect to chlorine remains higher than that obtained with the reference system.

TABLE 1

Ethylene-Propylene solution copolymerization: tests with AlEt$_2$Cl/CCl$_3$COOEt

| Examples | Catalyst | Al/V mol/mol | Ox./V mol/mol | Polymer gr. | Time min. | Yield V gr Pol/gr V | Yield Cl gr Pol/gr Cl | C3% mol I.R. | Mn ×1000 | Mw ×1000 | MWD |
|---|---|---|---|---|---|---|---|---|---|---|---|
| 1 comp. | V (acac)$_3$ | 50:1 | 6:1 | 36.1 | 60 | 16900 | 360 | 33.7 | 55 | 112 | 2 |
| 2 comp. | V (acac)$_3$ | 10:1 | 6:1 | 3.5 | 20 | 1600 | 80 | — | — | — | — |
| 1 | (II) | 50:1 | 6:1 | 50.2 | 60 | 23500 | 440 | 30.9 | 51 | 116 | 2.3 |
| 2 | (III) | 50:1 | 6:1 | 54.7 | 60 | 25600 | 520 | 28.8 | 79 | 150 | 1.9 |
| 3 | (IV) | 50:1 | 6:1 | 55.4 | 60 | 25900 | 500 | 27.4 | 76 | 145 | 1.9 |
| 4 | (V) | 50:1 | 6:1 | 57.5 | 30 | 27000 | 500 | 33 | 45 | 115 | 2.5 |

TABLE 2

Ethylene-Propylene solution copolymerization: tests with Al Trialky

| Examples | Catalyst | Al-alkyl | Al./V mol/mol | Polymer gr. | Time min. | Yield V gr Pol/gr V | Yield Cl gr Pol/gr Cl | C3% mol I.R. | Mn ×1000 | Mw ×1000 | MWD |
|---|---|---|---|---|---|---|---|---|---|---|---|
| 3 comp. | V (acac)$_3$ | Al(i-Bu)$_3$ | 50:1 | 0 | | | | | | | |
| 4 comp. | (I comp.) | Al(i-Bu)$_3$ | 50:1 | 3 | 60 | 1400 | 220 | 24.3 | 26 | 120 | 4.6 |
| 5 | (II) | AlEt$_3$ | 50:1 | 3.4 | 10 | 1600 | 250 | 27.7 | 26 | 194 | 7.4 |
| 6 | (II) | AlMe$_3$ | 50:1 | 8.7 | 10 | 4100 | 650 | 30.6 | 46 | 348 | 7.6 |
| 7 | (II) | Al(i-Bu)$_3$ | 50:1 | 8.3 | 10 | 3900 | 620 | 27.5 | 62 | 405 | 6.6 |
| 8 | (II) | Al(i-Bu)$_3$ | 50:1 | 38 | 60 | 17700 | 2800 | 20.5 | 36 | 416 | 11.5 |
| 9 | (II) | Al(i-Bu)$_3$ | 10:1 | 43.4 | 60 | 20300 | 3200 | 25.7 | 29 | 297 | 10.3 |
| 10* | (III) | Al(i-Bu)$_3$ | 50:1 | 4.7 | 60 | 2200 | 1050 | 20.9 | 16 | 180 | 11 |
| 11 | (IV) | Al(i-Bu)$_3$ | 10:1 | 48.5 | 60 | 22700 | 4600 | 26 | 26 | 335 | 13 |
| 12 | (V) | Al(i-Bu)$_3$ | 10:1 | 51.5 | 60 | 24000 | 3800 | 19.6 | 32 | 123 | 3.9 |
| 13 | (VI) | Al(i-Bu)$_3$ | 10:1 | 12.7 | 60 | 6000 | 1400 | 22 | | | |
| 14 | (VII) | Al(i-Bu)$_3$ | 10:1 | 64.5 | 60 | 30200 | 4800 | 18 | | | |

*catalyst aged with Al(i-Bu)$_3$ at 50° C. for 10 min.
Al/V = 5:1;
polymerization temperature: 50° C.

TABLE 3

Ethylene-Propylene solution copolymerization: tests with Al(i-Bu)$_3$CCl$_4$ (Al/V = 50:1)

| Examples | Catalyst | Ox./V mol/mol | Polymer gr. | Time min. | Yield V gr Pol/gr V | Yield Cl gr Pol/gr Cl | C3% mol I.R. | Mn ×1000 | Mw ×1000 | MWD |
|---|---|---|---|---|---|---|---|---|---|---|
| 3 comp. | V (acac)$_3$ | — | 0 | 0 | | | | | | |
| 5 comp. | V (acac)$_3$ | 25:1 | 5 | 60 | 2300 | 34 | 21.8 | | | |
| 7 | (II) | — | 8.3 | 10 | 3900 | 620 | 27.5 | 62 | 405 | 6.6 |
| 15 | (II) | 50:1 | 9.2 | 10 | 4300 | 30 | 28.8 | 34 | 269 | 8 |

TABLE 4

Ethylene-Propylene solution copolymerization: tests with V(CCl$_3$COO)$_3$ (THF)$_{0-2}$/Al(i-Bu)$_3$(Al/V = 10:1)

| Examples | Catalyst | THF/V | Polymer gr. | Time min. | Yield V gr Pol/gr V | Yield Cl gr Pol/gr Cl | C3% mol I.R. | Mn ×1000 | Mw ×1000 | MWD |
|---|---|---|---|---|---|---|---|---|---|---|
| 16 | (IIb) | 0 | 13.2 | 60 | 6200 | 1000 | 18 | | | |
| 9 | (II) | 1 | 43.4 | 60 | 20300 | 3200 | 25.7 | 29 | 297 | 10.3 |
| 17 | (IIa) | 2 | 33.5 | 60 | 15700 | 2500 | 23.4 | 73 | 388 | 5.3 |

TABLE 5

Ethylene-Propylene solution copolymerization: tests with V(CCl$_3$COO)$_3$ (THF)$_1$/Al(i-Bu)$_3$(Al/V = 50:1)

| Examples | Aging | Polymer gr. | Time min. | Yield V gr Pol/gr V | Yield Cl gr Pol/gr Cl | C3% mol I.R. | Mn ×1000 | Mw ×1000 | MWD |
|---|---|---|---|---|---|---|---|---|---|
| 8 | — | 38 | 60 | 17700 | 2800 | 20.5 | 36 | 416 | 11.5 |
| 18 | Al(i-Bu)$_3$/V = 3:1 | 23 | 60 | 10700 | 1700 | 20.8 | 36 | 290 | 8.1 |
| 19 | Al(i-Bu)$_3$/V = 1:1 | 25 | 60 | 11700 | 1900 | 22.7 | 51 | 300 | 5 |

The aging was carried out by putting the V complex in contact with the Al alkyl in toluene, at the ratio shown in the table, for 10 minutes at room temperature.

TABLE 6

Ethylene-Propylene copolymerization in liquid propylene

| Examples | Catalytic System | [V] mmol/l | Al/V mol/mol | ETA/V mol/mol | H$_2$ atm. | Yield V gr pol./gr. V | Yield Cl gr pol./gr Cl | C3% w I.R. |
|---|---|---|---|---|---|---|---|---|
| 6 comp. | V (acac)$_3$/AlEt$_2$Cl/ETA | 0.035 | 70 | 8 | — | 51500 | 800 | 47 |
| 21 | (IIa)/Al(i-Bu)$_3$ | 0.046 | 50 | — | — | 42300 | 6800 | 25 |
| 20 | (IIa)/Al(i-Bu)$_3$ | 0.046 | 50 | — | 1 | 28700 | 20 | 20 |

TABLE 7

Ethylene-Propylene-ENB terpolymerization in liquid propylene

| Examples | Catalytic System | [V] mmol/l | Al/V mol/mol | ETA/V mol/mol | H₂ atm. | ENB mol % | Yield V gr pol./gr. V | Yield Cl gr pol./gr Cl | C3% w I.R. | ENB w % |
|---|---|---|---|---|---|---|---|---|---|---|
| 7 comp. | V (acac)₃/AlEt₂Cl/ETA | 0.035 | 70 | 5 | — | 0,4 | 51500 | 800 | 47 | 3 |
| 8 comp. | V (acac)₃/AlEt₂Cl/ETA | 0.070 | 35 | 4 | — | 0,6 | 24600 | 700 | 41 | 3,5 |
| 22 | (IIa)/Al(i-Bu)₃ | 0.065 | 35 | — | — | 0,4 | 37900 | 6100 | 23 | 2,5 |
| 23 | (IIa)/Al(i-Bu)₃ | 0.065 | 35 | — | 1 | 0,4 | 16200 | 2600 | 25 | 3,7 |
| 24 | (IIa)/Al(i-Bu)₃ | 0.104 | 25 | — | — | 0,6 | 18700 | 3000 | 34 | 6,1 |
| 25 | (IIa)/Al(i-Bu)₃ | 0.104 | 25 | — | 1 | 0,6 | 11700 | 1900 | 30 | 7,2 |

What is claimed is:

1. A Vanadium complex having general formula (I)

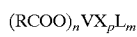

$$(RCOO)_n VX_p L_m \qquad (I)$$

wherein R is a monofunctional hydrocarbon radical having from 1 to 20 carbon atoms and from 1 to 6 halogen atoms, selected from chlorine and bromine; X is chlorine or bromine; L is an electron donor; p+n=3, 4 or 5; n is greater than or equal to 1; m is between 0 and 3.

2. The Vanadium complex according to claim 1, wherein R is a monofunctional hydrocarbyl radical containing from 1 to 6 chlorine atoms.

3. The Vanadium complex according to claim 1, wherein X is chlorine.

4. The complex according to claim 1, wherein n+p=3.

5. The complex according to claim 1, wherein R—COO is

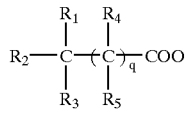

wherein $R_1$, $R_2$, $R_3$, $R_4$ and $R_5$, the same or different, are selected from H, Cl or Br, alkyls, cycloalkyls, aryls, arylalkyls, alkylaryls or alkyls, cycloalkyls, aryls, arylalkyls, alkylaryls containing chlorine or bromine, with the proviso that at least one of the $R_1$–$R_5$ residues is selected from chlorine or bromine, or an alkyl, cycloalkyl aryl, arylalkyl, alkylaryl group containing chlorine or bromine; q varies from 0 to 10.

6. The complex according to claim 1, wherein R—COO is

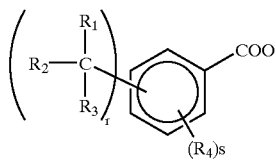

wherein $R_1$, $R_2$, $R_3$, $R_4$ have the meaning defined above, r and s vary independently from 0 to 5, with the restriction that r+s are less than or equal to 5.

7. The complex according to claim 1, wherein R—COO is

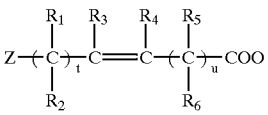

wherein:

Z, $R_1$, $R_2$, $R_3$, $R_4$, $R_5$, $R_6$ the same or different, are selected from H, Cl, Br, alkyl, cycloalkyl, aryl, arylalkyl, alkylaryl, alkyls, cycloalkyls, aryls, arylalkyls, alkylaryls containing chlorine or bromine, with the proviso that at least one of the Z and $R_1$–$R_6$ residues is chlorine or bromine or an alkyl, cycloalkyl aryl, arylalkyl, alkylaryl group containing chlorine or bromine;

t and u independently vary from 0 to 10, preferably from 0 to 2.

8. The complex according to claim 1, wherein R is selected from cycloalkyl, polycycloalkyl, cycloalkenyl, polycycloalkenyl having from 3 to 20 C atoms, substituted with chlorine or bromine or with hydrocarbyl groups containing chlorine or bromine.

9. A process for the preparation of the Vanadium complexes having general formula (I) which comprises:

a) reaction of a Tallium (Tl) salt having the general formula RCOOTl, wherein R has the meaning defined above, with a Vanadium halide, preferably VCl₃, in an aliphatic or aromatic, ether or chlorinated, hydrocarbon solvent, alone or in a mixture, preferably selected from THF and dimethoxyethane, at temperatures ranging from 0 to 50° C., preferably from 15 to 30° C., for a time ranging from 30 minutes to 6 hours, preferably from 1 to 4 hours;

b) separation, preferably filtration, of the Tl halide formed by the reaction;

c) isolation of the Vanadium complex.

10. A catalytic system for the copolymerization of α-olefins consisting of:

(a) Vanadium complex having general formula (I) according to claim 1;

(b) organo Aluminum derivative having general formula (II) $AlR_n X_m$, wherein R is a $C_1$–$C_{20}$ alkyl group, X is chlorine or bromine, and n+m=3, with the exclusion of the compound having n=0;

(c) optionally a reactivator.

11. The catalytic system according to claim 10, wherein X is chlorine.

12. The catalytic system according to claim 10, wherein the reactivator (c) is a chlorinated compound.

13. The catalytic system according to claim 10, wherein the Vanadium complex (I) has general formula (Ia) $(CCl_3-(-CH_2-)_n-COO)_3V$, wherein n is between 0 and 2.

14. The catalytic system according to claim 10, wherein the organo Aluminum derivative (II) has the general formula $AlR_3$, wherein R is a $C_1$–$C_{20}$ alkyl group.

15. The catalytic system according to claim 14, wherein R is isobutyl.

16. The catalytic system according to claim 14, wherein the reactivator is absent.

17. A process for the (co)polymerization of alpha-olefins in liquid phase, at low or medium pressure, at a temperature ranging from −5° C. to 75° C., wherein the above (co)polymerization is carried out in the presence of the catalytic system according to claim 10.

* * * * *

UNITED STATES PATENT AND TRADEMARK OFFICE
CERTIFICATE OF CORRECTION

PATENT NO. : 6,495,641 B1
DATED : December 17, 2002
INVENTOR(S) : Masi et al.

It is certified that error appears in the above-identified patent and that said Letters Patent is hereby corrected as shown below:

<u>Title page,</u>
Item [75], should read:
-- [75] Inventors: Francesco Masi, Sant' Angelo Lodigiano (IT); Liliana Gila, Cameriano (IT); Roberto Santi, Novara (IT); Antonio Proto, Novara (IT); Evelina Ballato, Crusinallo di Omegna (IT); Anna Maria Romano, Novara (IT); Paolo Biagini, Trecate (IT) --

Item [30], the Foreign Application Priority Data should read:
-- [30] Foreign Application Priority Data

Nov. 19, 1998 (IT) ………………..MI98A002499 --

Signed and Sealed this

Twentieth Day of May, 2003

JAMES E. ROGAN
*Director of the United States Patent and Trademark Office*